United States Patent
De La Mettrie (10) Patent No.: US 12,279,992 B2
(45) Date of Patent: Apr. 22, 2025

(54) USER GUIDANCE ASSISTANCE SYSTEM DIRECTING TOWARDS OR OBSERVING A DETERMINED ZONE OF INTEREST

(71) Applicant: PERIPHERAL, Bourges (FR)

(72) Inventor: Aymar De La Choue De La Mettrie, Vernon (FR)

(73) Assignee: PERIPHERAL, Bourges (FR)

( * ) Notice: Subject to any disclaimer, the term of this patent is extended or adjusted under 35 U.S.C. 154(b) by 19 days.

(21) Appl. No.: 18/251,453

(22) PCT Filed: Oct. 21, 2021

(86) PCT No.: PCT/FR2021/051844
§ 371 (c)(1),
(2) Date: May 2, 2023

(87) PCT Pub. No.: WO2022/096797
PCT Pub. Date: May 12, 2022

(65) Prior Publication Data
US 2023/0404809 A1  Dec. 21, 2023

(30) Foreign Application Priority Data
Nov. 5, 2020 (FR) .................................. 2011341

(51) Int. Cl.
*A61F 9/02* (2006.01)
*G01C 21/20* (2006.01)
(Continued)

(52) U.S. Cl.
CPC .............. *A61F 9/029* (2013.01); *G01C 21/20* (2013.01); *G02B 27/017* (2013.01); *G02B 27/34* (2013.01);
(Continued)

(58) Field of Classification Search
CPC ....... A61F 9/029; G01C 21/20; G02B 27/017; G02B 27/34; G02B 2027/0138; G08B 5/36
See application file for complete search history.

(56) References Cited

U.S. PATENT DOCUMENTS 4,730,104 A * 3/1988 Rogers ...................... G01S 7/06
356/145
10,012,506 B1 7/2018 Monahan et al.
(Continued)

FOREIGN PATENT DOCUMENTS

DE  102009060683 A1  1/2011
WO  2015020995 A1  2/2015
WO  2015038527 A1  3/2015

OTHER PUBLICATIONS

International Search Report from International Application No. PCT/FR2021/051844 dated Feb. 4, 2022, 3 pgs.
(Continued)

*Primary Examiner* — Nitin Patel
*Assistant Examiner* — Cory A Almeida
(74) *Attorney, Agent, or Firm* — Tutunjian & Bitetto, P.C.

(57) ABSTRACT

The invention relates to a guidance assistance system having a peripheral rim defining a peripheral field of vision and a guidance information display device on the peripheral rim. The guidance information display device includes light sources which can be controlled by a control unit. The display device includes a sensor of spatial information relating to a position and/or an orientation of the visualisation window and a circuit for processing the spatial information according to the zone of interest in order to determine guidance information. The control unit is configured to control the light sources on the basis of the guidance
(Continued)

information in order to display, in the field of vision, a direction to be followed by the user.

10 Claims, 7 Drawing Sheets

(51) Int. Cl.
*G02B 27/01* (2006.01)
*G02B 27/34* (2006.01)
*G08B 5/36* (2006.01)

(52) U.S. Cl.
CPC ........ *G08B 5/36* (2013.01); *G02B 2027/0138* (2013.01)

(56) References Cited

U.S. PATENT DOCUMENTS

| | | |
|---|---|---|
| 2014/0223647 A1 | 8/2014 | Long et al. |
| 2016/0223338 A1* | 8/2016 | Lassen ................. G02B 27/017 |
| 2017/0287441 A1* | 10/2017 | Mckendrick ............ G06F 1/163 |
| 2019/0293939 A1* | 9/2019 | Sluka ................. G02B 27/0172 |

OTHER PUBLICATIONS

Kiss Francisco, et al. "Clairbuoyance Improving Directional Perception for Swimmers" Proceedings of the 2019 CHI Conference on Human Factors in Computing Systems, May 4, 2019-May 9, 2019, pp. 1-12, ACM, 2 Penn Plaza, Suite 701 New York, NY 10121-0701 USA, May 2, 2019.

\* cited by examiner

USER GUIDANCE ASSISTANCE SYSTEM DIRECTING TOWARDS OR OBSERVING A DETERMINED ZONE OF INTEREST

TECHNICAL FIELD

The present invention relates to the field of guidance assistance systems.

The object of the present invention more particularly concerns a guidance assistance system for displaying visual information in real time to assist a user in observing a determined zone of interest or directing towards a determined zone of interest.

Zone of interest, within the meaning of the present invention, means throughout the following description any zone that is of interest for the user; it may be, for example, a final destination such as a meeting/assembly point, a finish line, a landing runway. It may also be a route, a predefined road or also one or more steps along a route or a predefined road. It may also be a target or a point or a person to be observed/monitored. Here, it will be understood that, generally, this zone of interest is defined by a set of spatial coordinates.

The present invention is advantageously applicable in the field of sport and particularly extreme sports or board sports such as, for example, skydiving, paragliding, downhill mountain-biking, skiing, automobile rallies, etc.

The present invention is also applicable in many other advantageous applications in other activities such as, for example, for driving a vehicle (aircraft or other) or for firefighter or military interventions in a hostile environment.

PRIOR ART

Offset interfaces are known in the prior art; these offset interfaces are located by definition outside of the field of vision of the user and require a head movement of the user to be consulted.

It is easily understood that the use of such interfaces is not possible for certain applications such as, for example, the practice of an extreme sport. Indeed, the athlete needs to be focused on their practice to avoid any accident; the same applies to a firefighter or a soldier during an operation because neither of them can use their hands to interact with the screen.

Other types of interfaces are known in the prior art that located within the field of vision of the user.

In aviation and more recently in the automotive field, such interfaces are in the form of "head-up display" devices, also known under the acronym HUD.

These head-up display devices more often integrate augmented reality display means that make it possible to provide additional information to the user such as, for example, extrinsic information concerning the environment of the vehicle.

The display of this extrinsic information often contributes to the safety of the vehicle and makes it possible for the driver or the pilot to understand the environment in which they evolve by improving their perception of the environment.

Thus, in the automotive field, certain Advanced Driver-Assistance Systems (ADAS) are already known, which are equipped with an on-board camera and that are configured to display on a screen, for example a head-up display or HUD screen, an element of the road environment such as, for example, a road sign of the road environment and/or a pictogram representing a vehicle circulating in front of said vehicle or a detected hazard.

Other helmets or goggles integrating a screen are also known such as, for example, those proposed in the documents EP3028121B1, FR3061312A1, FR3017966A1, US2003/0184868A1, U.S. Pat. No. 6,394,601B1 or also FR 2806312A1.

These devices therefore provide additional information either offset or superimposed on the field of vision of the user.

The principle of superimposing additional information in the field of vision of a user, however, makes the use of this type of device unsuitable for certain applications.

Indeed, the Applicant considers that intensive practice such as the practice of an extreme sport or an intervention by security forces requires simple and intuitive information to be provided for the user. This information must not obstruct the field of vision of the user and must be usable by the user without too much cognitive load. Indeed, explicit information, numbers, letters require the user to defocus from the activity on which they are concentrated.

Moreover, it is preferable for the helmet to be lightweight and small in order to avoid hindering the practice or creating problems or fatigue on the neck of the user.

It is also preferable for the computation times to be very short, this particularly in order to provide information in real time and guarantee good energy autonomy.

The Applicant considers respectfully that the solutions of the prior art are not satisfactory and do not offer an ergonomic and lightweight system, requiring few computer resources and providing the user with reliable and intuitive visual information without obstructing their field of vision or hindering the practice.

SUMMARY OF THE INVENTION

The aim of the present invention is to improve the above-described situation.

One of the objectives of the present invention is particularly to remedy the various above-mentioned drawbacks by proposing a user guidance assistance solution directing towards or observing a zone of interest.

To this end, the object of the present invention relates according to a first aspect to a user guidance assistance system directing towards or observing a determined zone of interest.

Advantageously, the system according to the present invention includes a visualisation window having a peripheral rim defining a peripheral field of vision of the user.

Advantageously, the system according to the present invention further includes a guidance information display device comprising a plurality of light sources extending at least partially along the peripheral rim of the visualisation window, the light sources being capable of being controlled independently of one another by a control unit.

Advantageously, the display device further comprises:
- at least one sensor configured to capture spatial information relating to a position and/or an orientation of the visualisation window in relation to the zone of interest; and
- a processing circuit configured to process the spatial information according to the zone of interest in order to determine user guidance information towards the zone of interest.

Advantageously, the control unit is configured to control (selectively) the light sources on the basis of the guidance information in order to display in the peripheral field of vision a direction to be followed by the user to direct towards or observe the zone of interest.

Preferably, the visualisation window is equipped with an optical visualisation screen (transparent). Optical visualisation screen means here an optical protection screen such as a visor and not a display screen.

Preferably, the display is carried out directly by the light points located in the peripheral rim of the visualisation window.

In another advantageous embodiment of the present invention, the optical visualisation screen is provided with etchings and/or inclusions formed in the screen, for example vertically and/or horizontally, to conduct the light emitted by the at least one light source on the screen, preferably towards the centre of the field of vision in such a way as to recentre the information so that it is less in the area of peripheral vision.

In an advantageous embodiment, it is preferably provided for that the control unit is configured to control the light sources in such a way as to form a virtual reticle (or another symbol) in the field of vision of the user.

Here, it is understood that the light sources are actuated selectively on the peripheral rim of the visualisation window in such a way as to interpose one in relation to the other to cross and form a virtual reticle in the axis of field of vision of the user, such a virtual reticle indicating with precision the direction/orientation of the target zone to be observed or reached.

Here, reference is made to a virtual reticle because the light sources here are on the peripheral rim of the visualisation window and do not come into the central axis of the field of vision of the user. The presence of light sources actuated selectively in the periphery makes it possible to form an unreal reticle that is perceived by the brain of the user by extrapolation of the light sources and that is fictitiously formed by the brain of the user in the field of vision without hindering the concentration and the vision thereof.

Preferably, the at least one sensor is a position sensor and/or an azimuth sensor and/or an inclination sensor and/or an accelerometer.

Thus, such a sensor makes it possible to recover information relating to the relative position of the visualisation window in relation to the zone of interest, the azimuth and/or the inclination of the visualisation window.

Advantageously, the display device comprises wireless communication means configured to communicate with an external entity in order to recover at least one item of external information relating to the external environment of the user.

Advantageously, the display device comprises acquisition means configured to acquire at least one item of status information of the system.

Preferably, the control unit is configured to control each light source in intensity and/or in colour.

Preferably, the plurality of light sources comprises an LED or OLED strip.

Preferably, the plurality of light sources comprises an optical fibre.

Correlatively, the object of the present invention relates according to a second aspect to a facial support intended to be worn directly or indirectly on the head of the user and comprising a guidance assistance system such as described above wherein the visualisation window is assembled integrally with said facial support.

Advantageously, the facial support consists of a pair of goggles, a mask or a helmet. Here, it is understood that the facial support may also be in the form of a visor, for example. Advantageously, the facial support is provided with at least one strap for holding in position said support on the head of said user.

Thus, the object of the present invention, due to its various functional and structural aspects described above, makes it possible to provide in real time reliable guidance information for the user to guide them or orient their gaze towards a predetermined zone of interest.

DESCRIPTION OF THE FIGURES

Other features and advantages of the present invention will become apparent from the description hereinbelow, with reference to FIGS. 1 to 9 that illustrate various non-limiting examples of embodiment thereof and wherein.

DESCRIPTION OF EXAMPLES OF EMBODIMENTS

A guidance assistance system 100 as well as the method associated therewith will now be described in the following together with reference to FIGS. 1 to 9.

The same elements are identified with the same reference signs throughout the following description.

As explained in the preamble, behaviours are becoming digitalised and increasingly take advantage of the recovery of data, in particular geo-located.

Yet, technologies known to date and making it possible to access augmented reality exclude users under stress the safety of which depends mainly on simple and intuitive information, such as for example, people practising an extreme sport or firefighters or security forces.

Indeed, the Applicant observes that a person practising an extreme sport such as, for example, skydiving or downhill mountain-biking, must be able to have reliable and easy to process information without being hindered in their practice, that is to say manipulate a dedicated object or focus on something other than their trajectory. This person must indeed focus on their practice and must be able to obtain simple information that primarily answers the following questions: "where must I go?", "where is the hazard?" and in some situations "where are the others?"

The Applicant considers that the head-up display (or HUD) devices and the augmented reality helmets are not adapted to these issues and particularly suffer from their high technicality; thus, the current solutions have the following drawbacks:

they need accurate settings (inter-pupil distance, binocular dioptre, etc.), they are heavy and bulky, they require energy, they are expensive, they are likely to shift from the axis of vision in the event of impacts and to propose erroneous guidance, they are sensitive to condensation, smoke, the presence of dust.

In addition, the Applicant considers that the solutions of the prior art do not make it possible to provide simple and usable information directly to the user to answer the above questions.

The system 100 proposed here within the scope of the present invention achieves this objective.

To achieve it, the underlying concept of the present invention is to orient the gaze and the practice of the user by exploiting the human reflexes of attention, and hypervigilance by embedding light points in the periphery of the field of vision of the user.

The use of the peripheral field of vision is characteristic of the present invention.

Such a use of the peripheral field of vision makes a peripheral visual awareness of the user possible, which is considered as the capacity of being aware without being distracted by a significant amount of information in relation to the particular scope and to the task to be accomplished.

On the physiological level, it is known that the area of peripheral vision represents 80% of the surface of the retina for 20% of optical cells. The peripheral field of vision therefore makes it possible to establish a vigilance process over a large portion of space, with a blurred and deficient vision of the light, without distracting from the primary task.

In addition, it is known that stressful situations (as is the use case in the case of the present invention) wakes up the nervous system which, among other things, causes the pupils to dilate. Such a dilation of the pupil therefore makes it possible for more light to enter and reach a larger area of the retina, which may provide a wider range of information about the environment.

Therefore, here it is the peripheral field of vision that it is sought to use to provide the user with simple and intuitive information without distracting them in their concentration.

Figure 1:
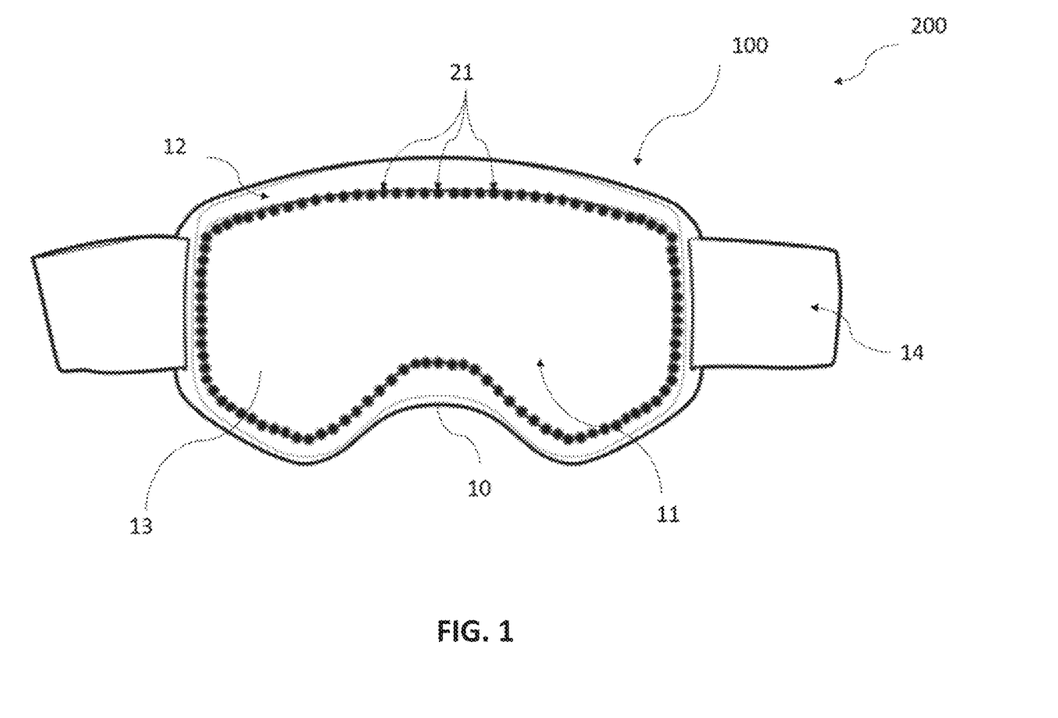
FIG. 1 shows a first schematic view of a guidance assistance system according to an example of embodiment of the present invention.
Figure 2:
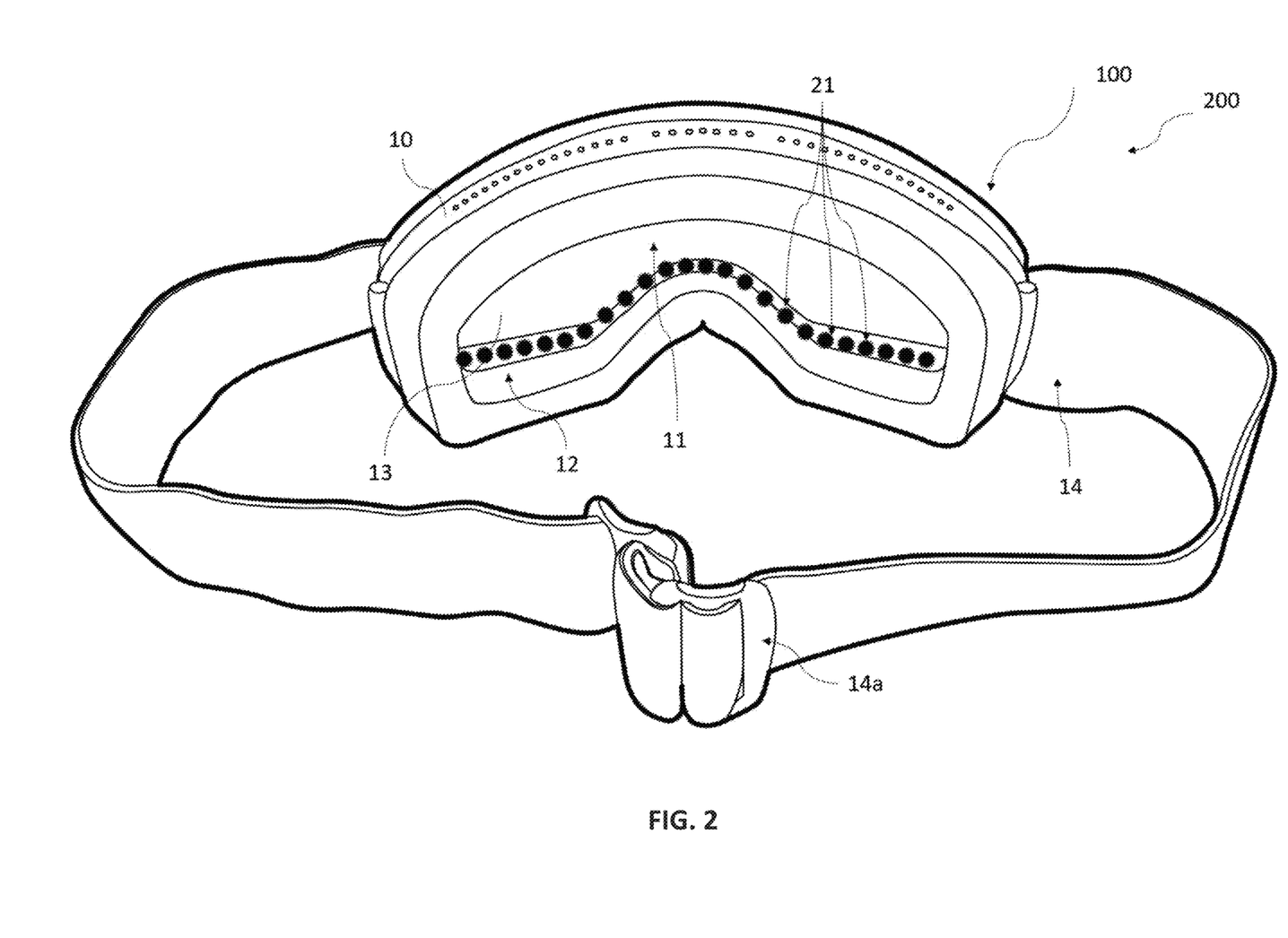
FIG. 2 shows a second schematic view of the guidance assistance system in accordance with FIG. 1.

The present invention provides in the example of FIGS. 1 and 2, which illustrate therein a particular and non-limiting example of embodiment of the invention, the implementation of a user U guidance assistance system 100 directing towards a zone of interest, noted here T (for "target").

This zone of interest T may correspond, for example, to a meeting or assembly point, a finish line, a step on a route, a particular point to be observed, a danger zone to be avoided, etc. Here, this zone of interest T is therefore defined by spatial coordinates that are known.

The system 100 comprises a device 10, here called display device, which includes an electronic board having at least one memory 27.

The coordinates of the zone of interest T are saved beforehand during a step S0 in this memory 27.

In this example, the at least one memory 27 corresponds, for example, to a volatile and/or non-volatile memory and/or comprises a memory storage device that may comprise the volatile and/or non-volatile memory, such as EEPROM, ROM, PROM, RAM, DRAM, SRAM, flash, magnetic or optical disc.

As previously stated, one of the objectives of the present invention is to provide easy-to-use information making it possible for the user U to be guided in real time and intuitively towards this zone of interest T without being hindered in the practice of their activity.

In this example and as illustrated in FIGS. 1 and 2, the system 100 integrated directly or indirectly into a facial support 200 being in the form of a mask, such as for example, a ski mask. In the example of FIG. 2, such a mask 200 is equipped with a strap 14 intended to hold the mask 200 in position around the head of the user U.

In this example, the strap 14 is furthermore provided with adjustment means 14a for adjusting the diameter of the strap 14 to adapt to the size of the head of the user U.

In this example, a conventional mask 200 is used, the general structure of which fits snugly to the anatomy of the face of the user U.

In this example, the system 100 integrated into the mask 200 therefore comprises a visualisation window 11 delimited by the peripheral rim 12 which corresponds here to the frame of the mask 200.

The peripheral rim 12 of this window 11 defines here the peripheral field of vision of the user U.

In this example, it is provided an optical visualisation screen 13, here a shield, covering the field of vision and for protecting the eyes of the user U.

Such a screen 13 may further comprise a demisting treatment, an anti-ultraviolet filter and/or an anti-reflection treatment to improve the comfort of the user.

In this example and as illustrated in FIGS. 1 and 2, the peripheral rim 12 is equipped with a plurality of light sources 21. These light sources 21 are therefore located in the periphery of the field of vision of the user U and are likely to hinder them in their perception of space. Therefore, they remain visible without obstructing the vision (that is to say without coming into the central axis of the field of vision of the user).

In the example illustrated in FIGS. 1 and 2, the light sources 21 extend at regular intervals along this peripheral rim 12.

Here, the light sources 21 are formed by an LED (Light-Emitting Diode) or OLED (Organic Light-Emitting Diode) strip.

Other types of light sources 21 may also be envisaged here by the person skilled in the art, such as for example, the optical fibre.

One of the underlying concepts of the present invention is to use these sources 21 to indicate outside of the main axis of the field of vision of the user U (but in the periphery thereof) the preferred direction to be followed to reach the zone of interest T.

This is made possible by an on-board intelligence in the system 100.

Figure 8:
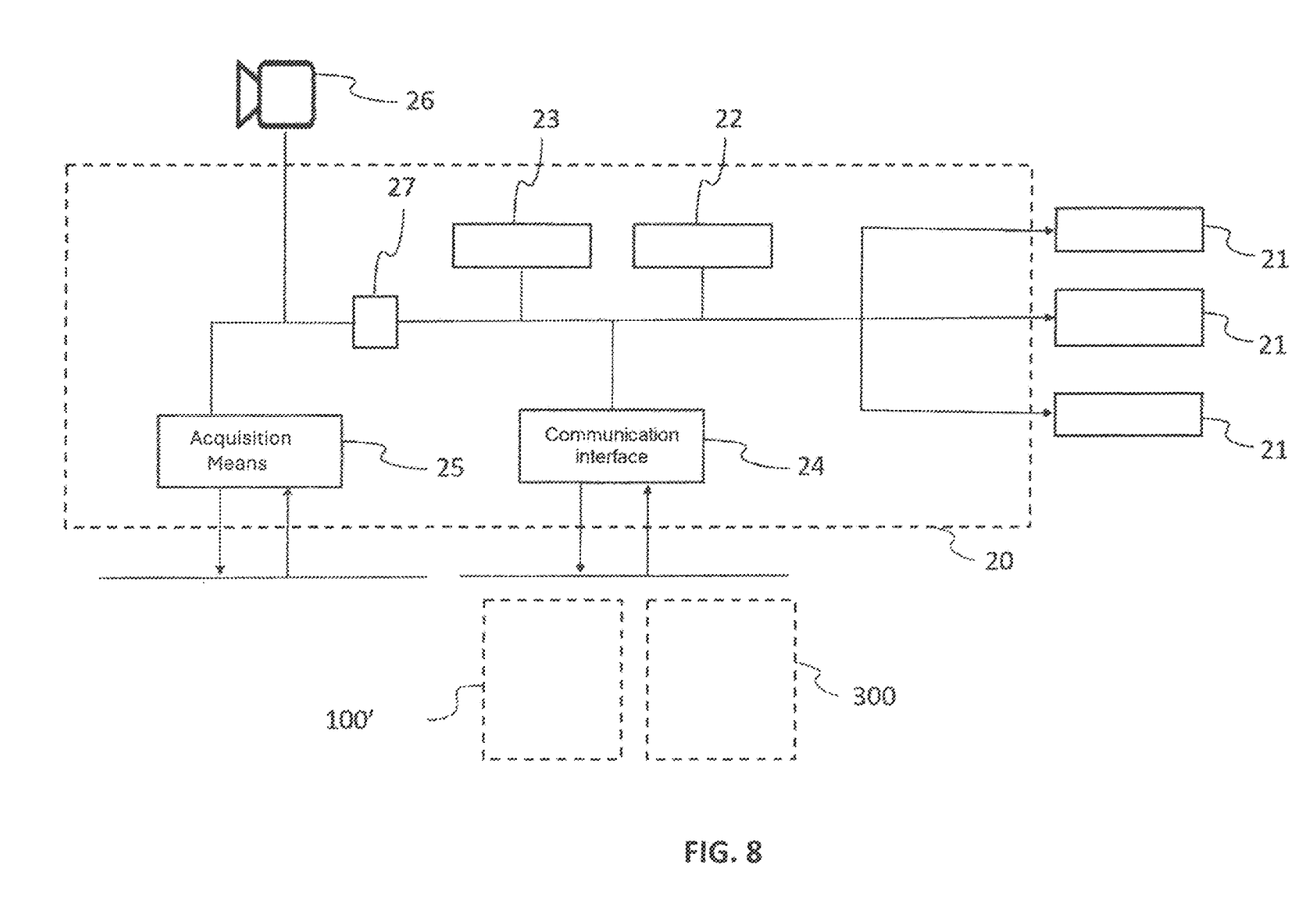
FIG. 8 schematically illustrates the guidance information display device integrated into the guidance assistance system according to a particular example of embodiment of the present invention.

This intelligence more particularly resides in the device 10 which comprises, without being limited thereto, an item of on-board electronic equipment such as an electronic computer (an ECU for "Electronic Control Unit", a smartphone, a tablet or also a laptop computer). The elements of the device 10, individually or combined, may be integrated into a single integrated circuit, into a plurality of integrated circuits, and/or into discrete electronic components. The device 10 may be produced in the form of electronic circuits or software (or computer) modules or also a combination of electronic circuits or software modules.

In this example, the device 10 comprises one (or more) processor(s) configured to execute instructions for performing the steps of the method and/or for executing the instructions of the on-board software in the device 10. The processor may include the integrated memory, an input/output interface and various circuits known by the person skilled in the art.

The computer code of the on-board software comprising the instructions to be loaded and executed by the processor is for example stored in the memory 27.

In the example described here, the device 20 further comprises a control unit 22 capable of controlling the sources 21 independently of one another.

Figure 9:
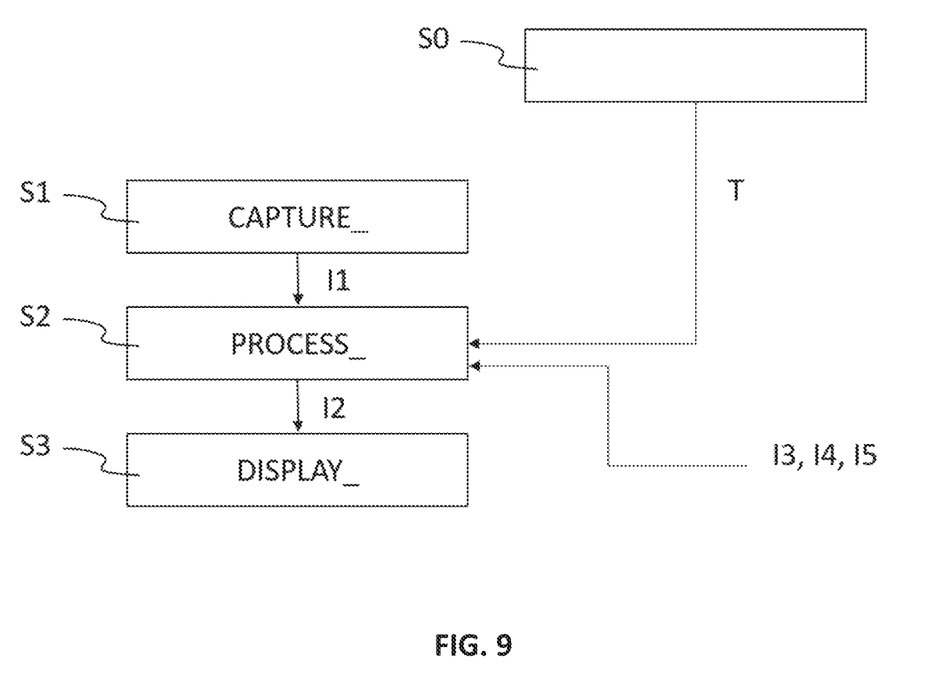
FIG. 9 illustrates an organisation chart of the various steps of a method implemented by a device in accordance with FIG. 8.

In this example, the integration of at least one sensor 23 such as an azimuth sensor, an inclination sensor and/or a position sensor is also provided. Such a sensor 23 is capable of capturing during a step S1 spatial information I1 relating to a position and/or an orientation of the visualisation window (11) in relation to said zone of interest T.

The sensor 23 therefore measures a value representative of the relative position of the mask (that is to say the inclination/orientation/position of the gaze of the user) in relation to the zone of interest T to be reached.

This spatial information I1 is subsequently transmitted to the processing circuit 24 (here, for example, a computer) which during a step S2 will process this spatial information I1 according to the zone of interest T (here the spatial coordinates of the zone of interest T saved in the memory 27) in order to determine guidance information I2.

The aim of this information I2 is to determine a guidance vector to orient the gaze of the user U in such a way that they observe or direct towards the zone of interest T.

This guidance information I2 is then sent to the control unit 22 so that it selectively controls each of the light sources 21 on the basis of this guidance information I2 in such a way as to, during step S3, display in the periphery of the field of vision of the user a direction to be followed so that the latter directs towards said zone of interest T.

Here, it is therefore understood that the light sources 21 will light up on the basis of this guidance information I2 determined by the processing circuit 24.

This selective control of the light sources 21 outside of the central axis of the field of vision of the user but in the periphery thereof makes it possible to guide the user U towards the zone of interest T without hindering them.

Figure 5:
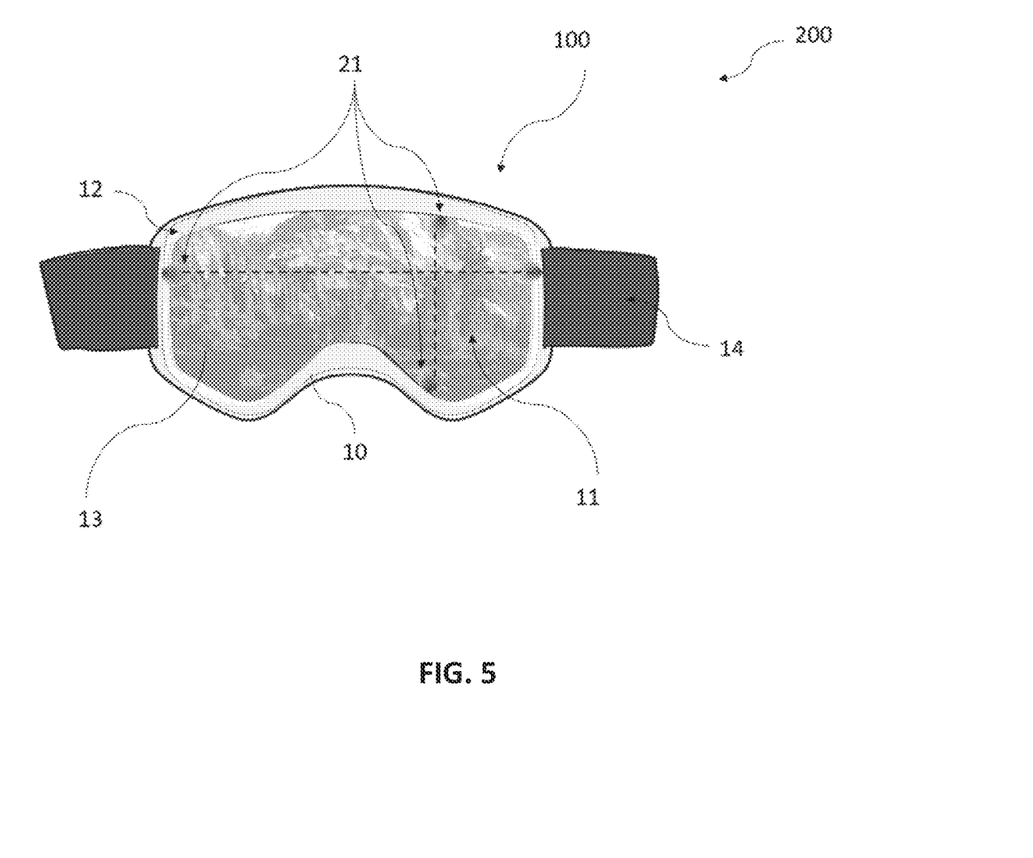
FIG. 5 shows a schematic view of a guidance assistance system forming a reticle in the field of vision of the user.
Figure 6:
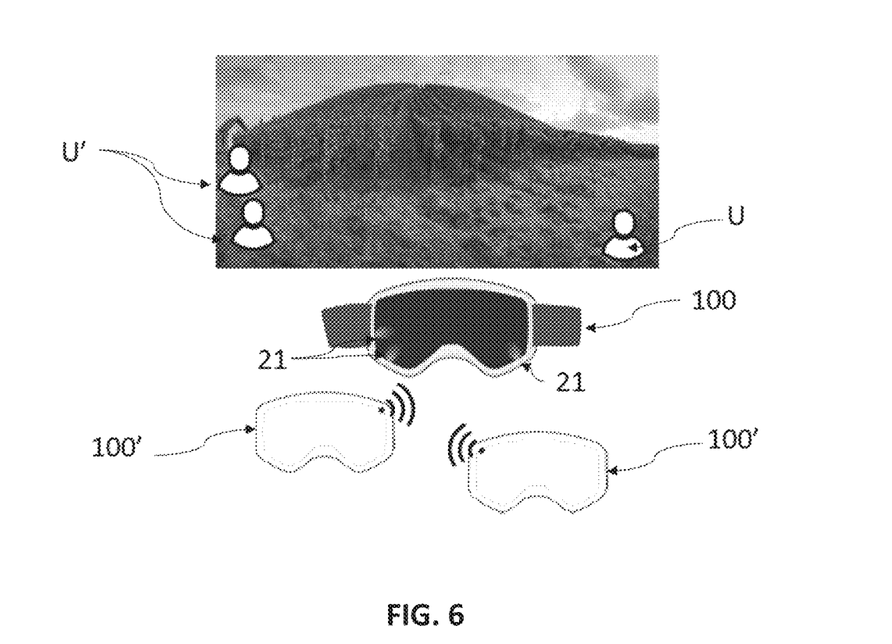
FIG. 6 shows a schematic view representing a use of a guidance assistance system according to the invention for the practice of an activity with a plurality of users.
Figure 7:
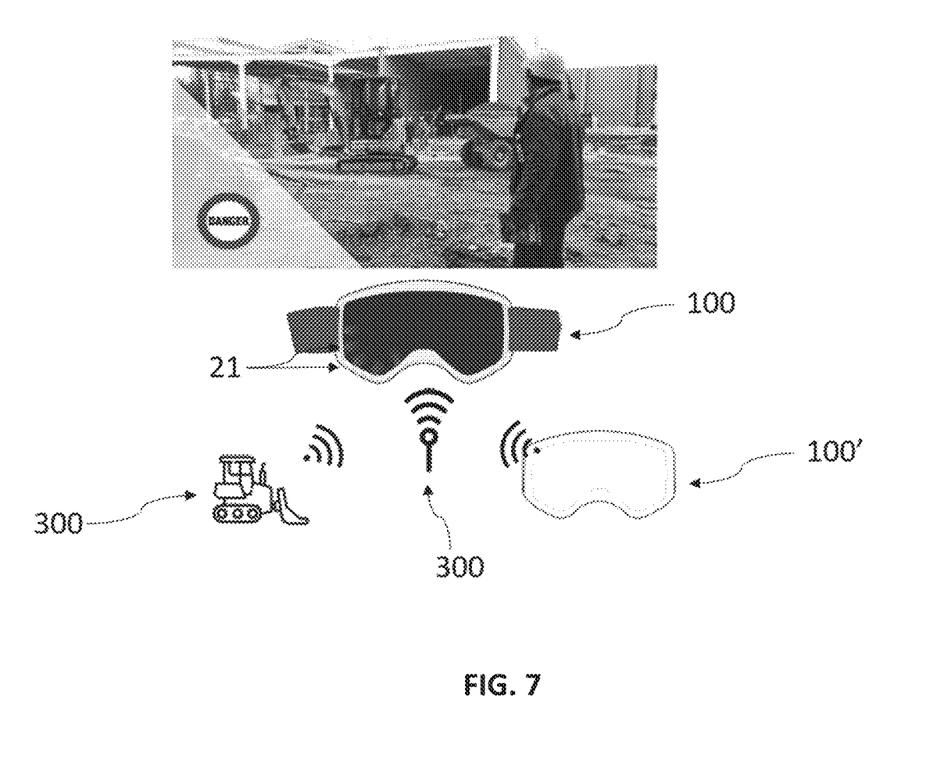
FIG. 7 shows a schematic view representing a use of a guidance assistance system according to the invention for a site comprising hazards.

Thus, as illustrated in FIG. 5, the light sources are actuated in the periphery of the field of vision of the user in such a way as to form a virtual reticle in the field of vision thereof. The latter only has to follow the direction provided by the virtual reticle by fixing their gaze towards the fictive crossing of two light beams formed by the two pairs of actuated light sources.

It is understood here that this information evolves in real time with the movement of the head and therefore of the central axis of vision of the user.

The display of simple visual information at the periphery of the field of vision of the user in the direction of the gaze and the position of the user is characteristic of the present invention.

The display of this information located in the area of peripheral vision makes it possible for the user to intuitively orient themselves in space.

Figure 3:
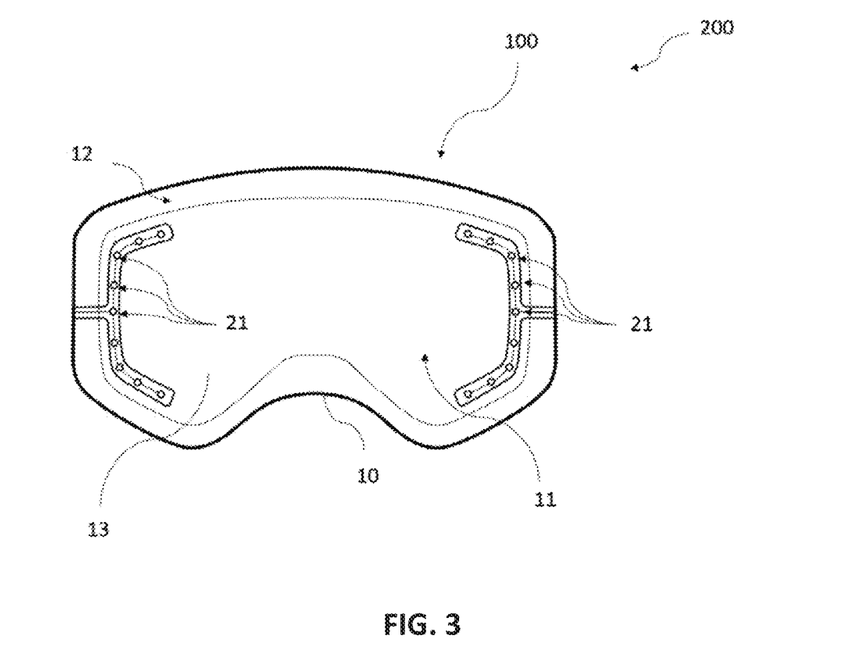
FIG. 3 shows a schematic view of a guidance assistance system according to another example of embodiment of the present invention.
Figure 4:
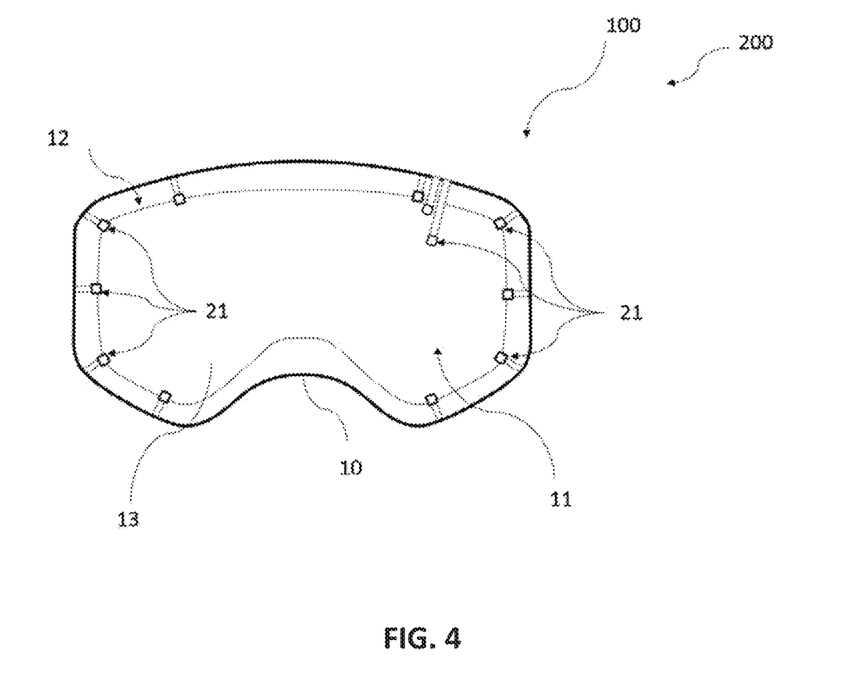
FIG. 4 shows a schematic view of a guidance assistance system according to another example of embodiment of the present invention.

A plurality of other examples of alternative embodiments are described and illustrated in FIGS. 3 and 4.

FIG. 3 shows all of the features of FIGS. 1 and 2 described above. The positioning and the arrangement of the light sources 21 are, however, very slightly different from the example of FIGS. 1 and 2.

Here, the light sources 21 are integrated directly into the screen 13.

These sources 21 are inserted into one or more layers and at various spacings of the central axis of vision between or on the various sheets constituting the screen 13.

In this example, the sources 21 only extend over the side edges of the screen 13 in such a way as to limit the overall dimension of the field of vision. It could be considered here that the sources 21 therefore remain in the periphery of the field of vision within the meaning of the present invention and do not come into the central axis of the field of vision.

In FIG. 4, another example of embodiment is also illustrated.

Therein, it is provided an inclusion of one or more sources 21 at a specific position, here for example, in the top left of the field of vision of the user U. Such an inclusion may be produced by one or more light guides of the optical fibre type and makes it possible to reflect the light towards the central axis of vision of the gaze of the user U. Such a light source 21 included in the screen 13 may carry information of important nature such as, for example, information relating to imminent danger.

In an advantageous embodiment not illustrated here, it is possible to form in the optical visualisation screen 13 straight etchings and/or inclusions formed for example vertically and/or horizontally in the screen 13 in order to conduct the light emitted by the at least one light source 21 on the screen 13.

Thanks to these etchings/inclusions arranged in the screen 13, it is thus possible to form in the field of vision of the user a real reticle in the axis of the field of vision of the user which makes it possible to guide the user with precision towards the zone T.

In order to enhance the visual information communicated to the user U, it is intended to provide other information and to keep into account the external environment (presence of a hazard for example) and any other users U' who are located close to the user U.

It is therefore provided to equip the device 20 with wireless communication means 24 in order to communicate with other external entities, for example another system 100' of another user U' (FIG. 6), a remote server, the cloud, an entity 300 such as, for example, a truck (FIG. 7) likely to represent a hazard or also a marker signalling a danger zone not to be crossed on a site. These communication means 24 are therefore capable of communicating with one or more external devices 100' and/or 300 and comprise one or more radio frequency RF interfaces, for example of the Bluetooth® or Wi-Fi®, LTE (Long-Term Evolution), LTE-Advanced type. Thus, data may for example be loaded towards the device 10 via the communication interface 24 by using a Wi-Fi® network such as according to IEEE 802.11, an ITS G5 network based on IEEE 802.11p or a mobile network such as a 4G (or LTE Advanced according to 3GPP release 10—version 10) or 5G network, particularly an LTE-V2X network.

The information 13 collected by the wireless communication means 24 is transmitted to the processing circuit 24 and is analysed to be taken into consideration in the determination of the guidance information I2. For example, the presence of a hazard or of an obstacle on the route of the user U may thus be taken into consideration to recalculate another route in order to reach the zone of interest T.

To secure the system, it is also possible to provide the integration of an additional camera 26 capable of capturing images I5 representative of the environment. These images I5 may subsequently be processed by image processing algorithms to detect a potential hazard or an obstacle.

It is also possible to provide the integration of one or more LIDAR(s) (Light Detection And Ranging) arranged on the helmet; a LIDAR sensor corresponds here to an optoelectronic system consisting of a laser emitter device, of a receiver device comprising a light collector (to collect the portion of the light ray emitted by the emitter and reflected by any object located on the route of the light rays emitted by the emitter) and of a photodetector that converts the collected light into an electrical signal; a LIDAR sensor thus makes it possible to detect the presence of objects located in the light beam emitted and to measure the distance between the sensor and each object detected, this in the aim of recovering points representing an obstacle or a hazard on the route of the user.

The information coming from this camera 26 or from the LIDAR(s) is sent directly to the processing circuit 24 for analysis and taken into consideration in the determination of the guidance information I2.

The information I3 and/or I5 coming from these wireless communication means 24 and/or from the camera 26 and/or from the LIDAR(s) may also be displayed directly on the peripheral rim 12 of the field of vision of the user by the actuation of one of the light sources 21.

Thus, for example, when an external hazard is detected (for example via the means 24 or the camera 26), it is possible to actuate a specific source such as, for example, that which is located by inclusion in the screen 13 (FIG. 4).

To secure the system, it is also possible to provide the integration of a microphone and/or of headphones capable of collecting or processing sounds. These sounds may subsequently be processed by processing algorithms configured to reduce the spurious noises, or to reinforce the spatial perception of a geo-referenced point.

In the example described here, it is also possible to control the light sources 21 in intensity and/or in colour. It is possible for example to emit in the field of vision a red light that flashes with a strong intensity to signal imminent danger.

Of course, this is one example from other possible examples.

The person skilled in the art will understand here that it is possible to provide according to the use case a plurality of scenarios and to programme the control of the light sources 21 according to the specific features of each practice and of each need.

Similarly, other information may be of interest and be communicated via the light sources 21 to the user U. Thus, in the example described here, the presence of acquisition means 25 is provided that are capable of recovering status information I4 of the system 100, such as for example, the status of the power supply battery or the level of wear of certain components to prevent a maintenance operation.

According to the coding of the information and the implementation of the display decision-making model, the device 100 is capable of displaying a plurality of different information according to various selectable modes.

For example, it is possible to provide the implementation of a remote control being for example in the form of a connected watch on the wrist of the user U (not shown here) which is capable via actuation on the touch screen of selecting the type of display to switch for example the system from a "guidance assistance/geolocation" mode making it possible to follow various meeting points along a predetermined route to an "equipment" mode making it possible to know the status of an item of equipment or also a "team" mode making it possible to know the relative position of other users U'.

Other display modes may also be envisaged to provide the user with reliable and easy-to-use information.

Thus, for example, it is possible to provide for an orientation especially far away from the cone of vision of the user, the actuation of a single light source to indicate the orientation towards which the user must make a movement to find the zone of interest.

When the zone T enters the cone of vision of the user, it is possible to provide the actuation of four light sources in lattice (FIG. 5) to indicate the direction of the point relative to that of the axis of the gaze with a virtual reticle.

Similarly, as previously stated, the intensity and/or the colour of all or part of the light sources may make it possible to signal other information such as, for example, the passage of the zone of interest. The variation of parameters relating to the intensity, to the colours and to the number of light sources 21 makes it possible to superimpose a plurality of information according to the use case.

Thus, the present invention makes it possible to overcome the various drawbacks of the prior art by making it possible to provide implicit information in the area of peripheral vision of the user.

The display of this information which does not appear in the main field of vision of the user but in the periphery thereof can be used directly by the user and does not require any reflection. Thanks to the on-board communication means in the system, this information may also be transmitted to other users.

The present invention is particularly intended in a non-limiting way for extreme sports, firefighters, industrial operators or also defence and security force agents during their interventions. Tourist and/or digital game applications as well as applications for learning or reinforcing capacities by interaction with the area of peripheral vision may also be envisaged.

It should be observed that this detailed description concerns a specific example of embodiment of the present invention, but that this description in no way applies any limiting nature to the object of the invention; on the contrary, it is intended to remove any inaccuracy or any incorrect interpretation of the following claims.

It should also be observed that the reference signs placed between parentheses in the following claims are in no way limiting; these signs are merely intended to improve the intelligibility and comprehension of the following claims as well as the scope of the protection sought.

The invention claimed is:

1. A user guidance assistance system directing towards or observing a determined zone of interest, said system comprising:
   a visualisation window having a peripheral rim defining a peripheral field of vision of said user and equipped with an optical visualisation screen defining a field of vision of said user, and
   a guidance information display device comprising a plurality of light sources extending at least partially along said peripheral rim of the visualisation window, said light sources being capable of being controlled independently of one another by a control unit, wherein said display device further comprises:

at least one sensor configured to capture spatial information relating to a position and/or an orientation of the visualisation window in relation to said zone of interest;

a processing circuit configured to process said captured spatial information according to the zone of interest in order to determine guidance information of said user towards said zone of interest;

said control unit being configured to control at least one of said light sources on the basis of said guidance information in order to form a virtual reticle in the field of vision of said user indicating a direction to be followed by said user to direct towards or observe said zone of interest, and wherein said optical visualisation screen is provided with straight etchings and/or inclusions formed in the screen to conduct the light emitted by the at least one light source on the screen.

2. The system according to any one of the preceding claims, wherein said at least one sensor is a position sensor and/or an azimuth sensor and/or an inclination sensor and/or an accelerometer.

3. The system according to claim 1, wherein said display device comprises wireless communication means configured to communicate with an external entity in order to recover at least one item of external information relating to the external environment of said user.

4. The system according to claim 1, wherein said display device-comprises acquisition means configured to acquire at least one item of status information of the system.

5. The system according to claim 1, wherein the control unit is configured to control each of the light sources-in intensity and/or in colour.

6. The system according to claim 1, wherein the plurality of light sources comprises an LED or OLED strip.

7. The system according to claim 1, wherein the plurality of light sources comprises an optical fibre.

8. A facial support intended to be worn directly or indirectly on the head of the user and comprising a system according to claim 1, wherein said visualisation window is assembled integrally with said facial support.

9. The facial support according to claim 8, which is in the form of a pair of goggles, a mask or a helmet.

10. The facial support according to claim 8, further comprising at least one strap for holding in position said support on the head of said user.

* * * * *